United States Patent [19]

Dawson et al.

[11] Patent Number: 4,772,427
[45] Date of Patent: Sep. 20, 1988

[54] POST-FOAMING GEL SHOWER PRODUCT

[75] Inventors: Andrew F. Dawson, Bolton; Bernard Moss, Tyldesley; Paul Wigglesworth, Levenshulme, all of United Kingdom

[73] Assignee: Colgate-Palmolive Co., New York, N.Y.

[21] Appl. No.: 127,126

[22] Filed: Dec. 1, 1987

[51] Int. Cl.$^4$ .................. C11D 1/83; C11D 17/00
[52] U.S. Cl. ..................... 252/559; 252/90; 252/174.17; 252/174.21; 252/550; 252/DIG. 5; 252/DIG. 13; 53/440; 220/85 B; 220/399
[58] Field of Search ............. 252/90, 92, 174.21, 252/174.17, 174, 173, 550, 559, DIG. 5, DIG. 13; 53/440, 526, 529; 220/3, 85 B; 222/399, 401, 406

[56] References Cited

U.S. PATENT DOCUMENTS

| | | |
|---|---|---|
| 2,995,521 | 8/1961 | Estignard-Bluard ............ 252/90 |
| 3,541,581 | 11/1970 | Monson .................. 252/90 |
| 3,705,855 | 12/1972 | Marschner ................ 252/90 |
| 3,728,265 | 4/1973 | Cella et al. .............. 252/90 |
| 3,962,150 | 6/1976 | Viola ................... 252/542 |
| 3,997,467 | 12/1976 | Jederstrom .............. 252/305 |
| 4,035,477 | 7/1977 | Schubert et al. ........... 424/47 |
| 4,405,489 | 9/1983 | Sisbarro ................ 252/315.4 |
| 4,528,111 | 7/1985 | Su .................... 252/107 |

FOREIGN PATENT DOCUMENTS 1021264 11/1977 Canada .
86/3405 6/1986 PCT Int'l Appl. .
1444334 7/1976 United Kingdom .

OTHER PUBLICATIONS

Croda, *Cosmetic/Pharmaceutical Formulary*, fifth edition of Cosmetic and Pharmaceutical Formulary, p. 48, 03/87.

Primary Examiner—Paul Lieberman
Assistant Examiner—Hoa Van Le
Attorney, Agent, or Firm—Richard J. Ancel; Murray M. Grill

[57] ABSTRACT

A stable, post-foaming gel shower product comprising a soap-free, surfactant-based gel composition consisting essentially of a major amount of water, about 3–23% by weight of a water-soluble anionic alkali metal $C_{10}$–$C_{16}$ alkyl ether sulfate surfactant, about 1–24% by weight of a water dispersible ethoxylated fatty alcohol or fatty ester, about 2–4% of isopropyl myristate, about 1–10% of a mono- or disaccharide and about 5–20% by weight of a saturated aliphatic hydrocarbon foaming agent having 4 to 5 carbon atoms as an integral part of the gel structure, the anionic surfactant and the ethoxylated fatty alcohol or ester being present in a weight ratio of 4:1 to about 1:4.

14 Claims, No Drawings

POST-FOAMING GEL SHOWER PRODUCT

FIELD OF THE INVENTION

This invention relates to a novel post-foaming gel based on an aqueous soap-free, surfactant-containing gel system, containing a 2:1 blend of n-pentane and iso-butane foaming agent as an integral part of the gel structure capable of producing increased volume and speed of foaming over conventional shower gels, and can be packaged in any form of barrier pack or container which will withstand pressure.

BACKGROUND AND PRIOR ART

Conventional skin cleansing liquid products and shower gels, are usually thick liquids, packed in bottles, which are relatively slow foaming and produce very little, relatively weak foam which quickly flattens. Post-foaming gels such as shaving gels, use a soap-based system which may optionally contain a minor amount of surfactant. Prior art post-foaming gel shower products consist of conventionally thickened sodium lauryl ether sulfate (SLES) and fatty acid diethanolamide (CDEA) blended together with a low level of foaming agent, such as the liquified hydrocarbon and chlorofluorohydrocarbon propellants. A number of major problems are associated with this type of product. The gel provides a stringy, tacky feel; possesses very poor high temperature stability; is restricted to very low levels of foaming agent due to the thinning effect of foaming agents on said thickened SLES/CDEA base, which results in non-optimization of foaming properties; and the need for high viscosity bases to allow for thinning effect on the base from the foaming agent while still retaining a good gel, provides process difficulties when handling such viscous bases.

It has now been found that all of the aforediscussed problems and limitations of previous post-foaming shower products have been overcome by present novel post-foaming gel which provides a post-foaming gel for shower use, with rapid development, of copious amounts of foam.

The use of an aqueous soap-based post-foaming gel in personal care products such as shaving creams, shampoos and skin cleansing products is well known in the art as disclosed in U.S. Pat. No. 2,995,521 wherein is disclosed a thick aqueous soap composition with a liquified aliphatic hydrocarbon foaming agent.

U.S. Pat. No. 3,541,581 discloses an aqueous, preferably soap-based post-foaming gel, which may contain a nonionic or anionic surfactant-either in addition to the soap or instead thereof and, optionally, a water soluble gelling agent, and a liquid post-foaming propellant packaged in an aerosol dispenser wherein the active ingredients are separated from the propellant by a collapsible bag to avoid undesirable premature foaming.

British Pat. No. 1,444,334, discloses post-foaming aqueous, soap-based shaving gel compositions containing 0.5-8% of a water-soluble hydroxy alkyl cellulose or polyoxyalkylene gelling agent and optionally a non-ionic or anionic surfactant; and 0.5-5% by weight of a post-foaming aliphatic and/or halogenated hydrocarbon agent; packaged in a conventional aerosol foam dispenser with a pressurized gas propellant in the head space to discharge the shaving gel.

U.S. Pat. No. 4,405,489 discloses a process and apparatus for the production of a stable aqueous post-foaming gel for packaging, based on an aqueous soap-containing or surfactant gel, preferably a soap based gel, and a post-foaming agent by intimately mixing and passing the mixture to a filling-machine for introduction into a container, using a continuous flow system under pressure and maintaining the mixture for a time and at a temperature and pressure sufficient to produce a post-foaming gel prior to the filling machine. A preferred additional ingredient is an oil sparingly soluble in water, such as a nonvolatile oily hydrocarbon and/or a liquid fatty alcohol and/or a fatty ester. The post-foaming gel comprises 40-80% water, 10-25% soap and 1.5-4% post-foaming agent, and about 0.25-1.5% oil.

Canadian Pat. No. 1,021,264 discloses anhydrous self-foaming shampoo compositions comprising 10-80% organic solvent (trichlorofluoromethane), which also functions as the foaming agent, 10-50% anionic or cationic surfactant and 0.1-15% of a film forming resin insoluble in water (methacrylate polymers, etc.), dispensed from a container as a liquid which forms a copious foam, when applied to wet hair at a temperature of about 75 degrees F. and above.

High-foaming anhydrous liquid detergent compositions, for use as shampoos, is also disclosed in U.S. Pat. No. 3,728,265, containing 10-25% of a liquified aliphatic hydrocarbon or halogenated hydrocarbon (propane, butane, etc.) dissolved in 10-25% organic solvent such as propylene glycol (water soluble), 30-45% anionic surfactant and 5-25% $C_6$-$C_{12}$ fatty acid alkanolamide, packaged in a non-pressurized container, which produces profuse foam when mixed with water.

U.S. Pat. No. 3,705,855 discloses a pressurized water-in-oil emulsion which reverses to a stable oil-in-water emulsion and can foam a finite time after discharge from an aerosol container to be used as a shaving cream, said emulsion comprising two immiscible liquids in emulsified form having water in the dispersed phase and propellant in the continuous phase. The ingredients in the emulsion include a water-in-oil emulsifier such as sorbitan fatty acid esters, and nonionic and/or anionic water soluble surfactants.

U.S. Pat. No. 3,962,150 discloses an aerated, low density (0.01-0.10 gm/ml) aqueous, non-pressurized, foam-producing, skin cleansing composition consisting of anionic and nonionic surfactants, 1-15% of an alcoholic solvent and 70-98% water, and having a viscosity of 0.5 to 300 cps. The foam is extruded from the dispenser by squeezing the container causing the aqueous solution to leave the reservoir and enter an air-mixing or foaming chamber via an internal dip tube, wherein the foam is produced and passed through a homogenizing element to provide a foam of a uniform consistency when discharged from the container.

None of the aforesaid prior art discloses a post-foaming gel shower product based on an aqueous soap-free, surfactant-containing gel system containing an anionic alkali metal $C_{10}$-$C_{16}$ alkyl ether sulfate surfactant, a water dispersible nonionic ethoxylated fatty alcohol or fatty ester, and about 5-20% by weight of a 2:1 blend of n-pentane and iso-butane foaming agent as an integral part of the gel structure. The anionic surfactant and the ethoxylated fatty alcohol or ester are present in a weight ratio of about 4:1 to about 1:4.

SUMMARY OF THE INVENTION

It has now been found that the base of the novel gelling system of the invention, which consists of an anionic alkali metal $C_{10}$-$C_{16}$ alkyl ether sulfate surfactant, a water dispersible nonionic ethoxylated fatty alcohol or fatty ester, and optionally preferred mono- or disaccharide, has a relatively thin viscosity, on the order of 100-1000 cps, prior to the addition of the foaming agent. Contrary herewith, previous post-foaming gels have had base viscosities as high as 30,000 to 35,000 cps to allow for thinning action of the foaming agent.

A major advantage of this invention over previous post-foaming shower products is that the foaming agent forms an integral part of the gel structure and has no thinning effect. This means that no limitation is placed on the level of foaming agent that may be used, which is essential in order to optimise foaming characteristics.

Accordingly, a primary object of the present invention is to prepare a post-foaming shower gel with a new gel system based on an aqueous soap-free, surfactant-containing composition and a 2:1 blend of n-pentane and iso-butane foaming agent as an integral part of the gel structure.

Another object of present invention is to provide a clear, or opaque ringing to soft post-foaming gel for shower use, with rapid development of a copious amount of foam.

Still another object of this invention is to provide a post-foaming gel having good high and low temperature stability.

Another object of this invention is to provide a stable post-foaming gel having good skin feel characteristics.

Another object of this invention is to provide a post-foaming gel which can be packaged in any form of container which will withstand pressure.

Still another object of this invention is to provide a post-foaming gel which ends the need for an outer propellant and is more conducive for shower use.

Additional objects, advantages and novel features of the invention will be set forth in part in the description which follows, and in part will become apparent upon examination of the following specification or may be learned by practice of this invention.

To achieve the foregoing and other objects in accordance with the present invention as embodied and broadly described herein, the novel, stable, high foaming post-foaming gel shower product of this invention comprises a soap-free, surfactant-based gel composition consisting essentially of a major amount of water, about 3-23% by weight of an anionic alkali metal $C_{10}$-$C_{16}$ alkyl ether sulfate surfactant, about 1-24% by weight of a water dispersible nonionic ethoxylated fatty alcohol or fatty ester, and about 5-20% by weight of a saturated aliphatic hydrocarbon foaming agent having 4 to 5 carbon atoms as an integral part of the gel structure. The anionic surfactant and the ethoxylated fatty alcohol or ester are present in a weight ratio of about 4:1 to about 1:4. Optionally preferred ingredients are about 1-10% of a mono- or disaccharide, and about 2-4% isopropyl myristate. More specifically, the post-foaming gel composition of present invention comprises a thin liquid base consisting essentially of, by weight, about 60-75% water, about 4-26% anionic alkali metal $C_{10}$-$C_{16}$ alkyl ether sulfate surfactant, about 1-25% of water dispersible nonionic ethoxylated fatty alcohol or fatty ester, gelled with a hydrocarbon foaming agent preferably in the weight ratio of 90% base to 10% foaming agent. A preferred foaming agent consists of a 2:1 blend of n-pentane and iso-butane. The anionic surfactant and the ethoxylated fatty alcohol or ester are present in a weight ratio of about 4:1 to about 1:4.

The described post-foaming gel products are stable at elevated temperatures, are firm, clear or opaque ringing to soft gels with significantly improved rapid development of foam in copious amounts; and can be packaged in any form of barrier pack or container which will withstand pressure such as a plastic container with an inflatable rubber bag inside, which forms a self-pressurized spray container. This terminates the need for an outer propellant and is more conducive for shower use.

DETAILED DESCRIPTION OF THE INVENTION

The major essential component of this post-foaming shower gel is about 60-75% water by weight of the gel base which may be deionized or distilled water. The water component is essential in the preparation of present stable shower gel having superior foaming properties and capable of being readily rinsed from the skin. The water possesses adequate compatibility with the other essential ingredients in the post-foaming gel composition.

An essential ingredient in present surfactant-based gel which is soap-free is a water soluble anionic alkali metal $C_{10}$-$C_{16}$ alkyl ether sulfate surfactant in an amount of about 3-23% by weight of the total composition, and preferably about 4-26% by weight of the gel base (minus the foaming agent). The preferred anionic surfactant is sodium lauryl ether sulfate which is defined as a sodium salt of sulfated ethoxylated lauryl alcohol conforming generally to the formula:

$$CH_3(CH_2)_{10}CH_2(OCH_2CH_2)_n OSO_3 Na$$

where n averages between 1 and 4 and is preferably 2.

Gels have been prepared with a base consisting of 25 to 28% SLES (2EO) and water, and gassed with a hydrocarbon blend in the ratio of 90% base to 10% 2:1 blend. Although gels have formed they have been relatively soft and weak and have taken up to 168 hours (7 days) to develop. Below 25% SLES (2EO) no gelling occurs. By increasing the number of moles of ethylene oxide on the SLES it is possible to reduce the level of SLES. While these high concentrations of SLES produce gels, they provide no skin feel, are relatively harsh, which may produce problems with irritancy and have poor relative stability within the container. Thus, the inclusion of additional materials is necessary to develop a marketable product.

Another essential ingredient in present gelling system of surfactant containing post-foaming gels is a water dispersible nonionic ethoxylated fatty alcohol or fatty ester in an amount of about 1-24% by weight of the total composition, and preferably about 1-25% by weight of the gel base. Above 25%, the ungassed liquid base develops a soft gel structure on standing which leads to process difficulties. No restriction is placed on the degree of ethoxylation. Suitable chemicals from the above classifications should be either partially insoluble/soluble or dispersible in water. Materials which are completely soluble at all temperatures or completely insoluble at all temperatures do not form satisfactory gels. Typical examples of water dispersible nonionic ethoxylated fatty alcohols and fatty esters which form gels include polyoxyethylene (4) lauryl alcohol (Brij 30), polyoxyethylene (20) soribtan monostearate (Tween 60), polyoxyethylene (20) sorbitan trioleate (Tween 85), polyoxyethylene sorbitan mono-oleate (Tween 81), polyoxyethylene sorbitan monolaurate (Tween 21), polyoxyethylene glycerol monolaurate (Tagat L2), polyoxyethylene glycerol mono-oleate (Tagat 02), polyoxyethylene glycerol castor oil (Tagat R60), polyethylene (6000) glycol (PEG 6000), polyoxyethylene (40) sorbitol septaoleate (Arlatone T), polyoxyethylene sorbitol hexaoleate (Atlas G 1086), and an ethoxylated lanolin alcohol. An ethoxylated lanolin alcohol is defined as the polyethylene glycol ether of lanolin alcohol with an ethoxylation value of 5 to 75. The preferred ethoxylated lanolin alcohol is the polyethylene glycol ether of lanolin alcohol with an ethoxylation value of 15, also known and commercially available as Polychol 15 by the Croda Company. It is a solid product which melts when heated at a temperature of 60-65 degrees C. in an aqueous medium. The presence of this water dispersible nonionic ingredient provides the skin with a good soft feel, improved stability as well as improved gel structure and rate of gelling.

The final essential ingredient in the soap-free, aqueous post-foaming surfactant-based gel of present invention is a post-foaming agent in an amount of about 5-20% by weight of saturated aliphatic hydrocarbons having from 4 to 5 carbon atoms selected from the group consisting of n-butane, iso-butane, n-pentane, iso-pentane, and preferably mixtures thereof. The preferred foaming agent is a 2:1 blend of n-pentane and iso-butane. N-pentane is a colorless liquid, having a density of 0.634 and a boiling point of 36 degrees C. Iso-pentane is also a colorless liquid, has a density of 0.622 and a boiling point of 30 degrees C. N-butane is a colorless gas having a boiling point of 1 degree C. Iso-butane is also a colorless gas having a boiling point of −11 degrees C. The addition of the hydrocarbon foaming agent to the liquid base, which does not gel on prolonged standing, develops a gel structure. A microemulsion is formed with the hydrocarbon foaming agent blended in the base material. The foaming agent is an integral part of the gel structure, therefore has no thinning effect on the gel as in prior art post foaming gels. Consequently, the need to limit the amount of the foaming agent to low levels in the formation of a post-foaming gel has been eliminated. Accordingly, no limitation is placed on the level of foaming agent used, which is essential in order to optimize foaming characteristics. The preferred ratio of foaming agent to the gel base is 10% to 90% by weight of the finished product.

A desirable additive in present gel system is a mono- or disaccharide such as fructose, galactose, sucrose and glucose in an amount of about 1-10% by weight of the composition. A monosaccharide is a hexose or pentose, in general an aldehyde-alcohol or ketone-alcohol such as sorbitol. A disaccharide is a carbohydrate yielding 2 monosaccharides on hydrolysis, such as lactose. Sorbitol is a hexahydric alcohol having the formula $C_6H_{14}O_6$, is in the form of colorless crystals having a melting point of 111 degrees C. and is soluble in water. It is a hygroscopic compound which functions as a humectant, to ensure the absorption of a certain amount of atmospheric moisture by the surfactant-based gel of present invention, and increases the gel formation rate.

Another preferred additive in present gel base is isopropyl myristate in the amount of about 2-4% by weight of the gel base, which is defined as an ester of isopropyl alcohol and myristic acid and conforms generally to the formula:

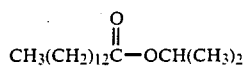

The commercial product usually appears as a mixture of myristate with small amounts of esters of palmitic and other saturated fatty acids. It is a practically odorless, liquid of low viscosity, solidifies at about 3 degrees C., is practically insoluble in water, but soluble in organic solvents and in ethanol, acetone, mineral oil, etc. It dissolves many waxes, cholesterol and lanolin, and is readily absorbed through the skin.

The coaction of the aforedescribed essential components unexpectedly provides a post-foaming gel shower product which optimizes foaming characteristics both as to increased volume and speed of foaming, and provides high temperature stability and a smooth, pleasant feel to the skin, and simplifies packaging of the product. The present novel post-foaming shower gel has overcome a number of major problems associated with this type of product. The omission of a single component adversely effects the unique properties of the total composition. Accordingly, the criticality of the essential ingredients and the specificity of each ingredient is necessary in the formulation of the present novel post-foaming shower gel product.

An in vitro method of producing foam, which is as close as possible in texture and volume to the foam created in normal use of the shower gel, shows that a maximum foam volume of 165 cm$^3$ is generated after approximately 40-45 seconds using a 10 gm sample of the gel of Example 2, hereinafter disclosed, as set forth in Table I. The method used comprises placing 10 g of gel in the centre of a fixed lower polystyrene disc, 20 cm in diameter and preferably 2.5 cm thick, held stationery on a lab jack. An upper movable similar polystyrene disc is attached to the shaft of a laboratory stirrer, set to 120 rpm. The movable upper disc is lowered until the gap between the upper and lower disc is 4 mm and is rotated for 45 seconds. The results are shown in Table I.

TABLE I

| TIME OF DISC | RUN | | | |
|---|---|---|---|---|
| ROTATION (SECS) | (1) | (2) | (3) | MEAN |
| 30 | 140 cm$^3$ | 140 cm$^3$ | 140 cm$^3$ | 140 cm$^3$ |
| 35 | 140 | 165 | 140 | 148.3 cm$^3$ |
| 40 | 165 | 165 | 165 | 165 cm$^3$ |
| 45 | 140 | 165 | 165 | 156.6 cm$^3$ |
| 50 | 165 | 165 | 165 | 165 cm$^3$ |
| 60 | 165 | 165 | 165 | 165 cm$^3$ |
| 70 | 165 | 165 | 165 | 165 cm$^3$ |
| 80 | 165 | 165 | 165 | 165 cm$^3$ |
| 90 | 165 | 165 | 165 | 165 cm$^3$ |
| 100 | 140 | 165 | 165 | 156.6 cm$^3$ |
| 110 | 190 | 165 | 190 | 181.6 cm$^3$ |
| 120 | 165 | 165 | 165 | 165 cm$^3$ |

This table clearly shows that a substantial amount of foam (140 cm$^3$) is generated after 30 seconds of shear, which increases in 40 seconds to 165 cm$^3$ and lasts at said level for 120 seconds. It may be found that certain gels require slightly longer shear times to produce a satisfactory foam due to the varying levels and types of foaming agent used in various gels. For example, a gel containing a foaming agent with relatively low volatility will require a greater amount of work to bring about foaming.

The density of the finished gel is approx. 1.000 gcm$^{-3}$. There is therefore, an approx. 16 fold increase in volume upon shearing the gel to its max.

However, the speed at which the max foam volume is achieved can be varied via adjustment of the hydrocarbon foaming agent type and quantity.

Foam development time can be controlled by adjustment of the hydrocarbon foaming agent type and level and also via adjustment of the formulation to generate a softer or a stiffer gel. A preferred gel consists of a gel which on extrusion from the package will begin to foam slightly, almost immediately. Complete foam generation does not take place until the gel is subject to shear. Although foam characteristics are variable and can be controlled relatively easily by additives or hydrocarbon foaming agent level, an approx. foam profile is as follows:

Density of foam: 0.09 gcm$^{-3}$
Viscosity of foam: 11.500 cps (sp TB at 5 rpm).

Foam is produced by the method described above for form generation. Foam density is measured by placing foam in a small plastic cup of known weight and volume. The foam is levelled to the top of the cup with a palette knife and the full cup weighed. Foam density is then calculated in the normal way.

Foam viscosity is measured on foam, as generated above, using the Brookfield RVT Heliopath viscometer in the normal manner at a temperature of 20–25 degrees C. (T-bar spindle 36 mm, at 20 rpm). The foam should be soft and uniform throughout with relatively open texture yet still perceivable as creamy (unlike a soap derived foam with a tight, very rich texture). Due to the nature of the product, in that it foams immediately upon shearing, it is very difficult to accurately measure the gel viscosity. An approx. viscosity lies between the range of 20,000 to 100,000 cps.

The above in vitro evaluation test for the foaming shower gel is not suitable for conventional shower gels. However, in vivo shower testing comparing the foaming shower gel against a conventional shower gel has shown significantly more foam and speed of foaming from foaming shower gel than with conventional shower gel, as shown in Table II and Table III using a scale of 0–10.

TABLE II

| Properties | MEAN A | B | T | SIG |
|---|---|---|---|---|
| 1. Spreadability of gel | 6.76 | 5.33 | 1.97 | n.s. |
| 2. Speed of foaming | 6.85 | 2.76 | 6.37 | sig @ <0.1% |
| 3. Amount of foam produced | 6.42 | 2.57 | 6.97 | sig @ <0.1% |
| 4. Feel on skin during bathing | 6.61 | 3.71 | 5.68 | sig @ <0.1% |
| 5. Creaminess of foam produced | 6.61 | 2.71 | 7.93 | sig @ <0.1% |
| 6. Lasting properties of foam | 5.47 | 2.71 | 5.4 | sig @ <0.1% |
| 7. Perseverence of foam generation | 5.38 | 2.95 | 4.85 | sig @ <0.1% |
| 8. Strength of fragrance during use | 5.28 | 4.23 | 1.63 | n.s. |
| 9. Ease of rinsing | 6.38 | 5.42 | 1.05 | n.s. |
| 10. Feel of skin after bathing | 6.00 | 4.61 | 2.18 | sig @ <5% |
| 11. Stickiness of skin after drying | 3.47 | 2.38 | 1.62 | n.s. |
| 12. Softness of skin after drying | 5.38 | 4.47 | 1.33 | n.s. |
| 13. Smoothness of skin after drying | 5.66 | 4.66 | 1.49 | n.s. |
| 14. Freshness of skin after drying | 5.61 | 4.33 | 2.03 | n.s. |

A - Foaming Shower Gel
B - Conventional Shower Gel

TABLE III

| Properties | MEAN A | B | T | SIG |
|---|---|---|---|---|
| 1. Spreadability of gel | 6.85 | 5.15 | 2.74 | sig @ <2% |
| 2. Speed of foaming | 7.4 | 2.4 | 9.13 | sig @ <0.1% |
| 3. Amount of foam produced | 6.65 | 2.09 | 7.27 | sig @ <0.1% |
| 4. Feel on skin during bathing | 6.65 | 4.65 | 4.53 | sig @ <0.1% |
| 5. Creaminess of foam produced | 7.3 | 2.25 | 8.6 | sig @ <0.1% |
| 6. Lasting properties of foam | 5.8 | 2.15 | 5.65 | sig @ <0.1% |
| 7. Perseverence of foam generation | 5.7 | 2.2 | 5.63 | sig @ <0.1% |
| 8. Strength of fragrance during use | 5.05 | 4.05 | 2.15 | sig @ <0.1% |
| 9. Ease of rinsing | 6.15 | 6.2 | 0.1 | n.s. |
| 10. Feel of skin after bathing | 5.6 | 5.7 | 0.35 | n.s. |
| 11. Stickiness of skin after drying | 3.15 | 3.4 | 1.1 | n.s. |
| 12. Softness of skin after drying | 5.85 | 5.95 | 0.49 | n.s. |
| 13. Smoothness of skin after drying | 5.95 | 6.25 | 0.92 | n.s. |
| 14. Freshness of skin after drying | 6.1 | 5.85 | 0.73 | n.s. |

A - Foaming Shower Gel
B - Conventional Shower Gel (Alternative Mild Formulation)

The post-foaming shower gel of this invention also may contain minor amounts of conventional additional components to impart any desired characteristic, which are compatible with the gel and do not adversely affect the gel structure. Suitable additives include coloring agents, perfumes, preservatives, antiseptic agents and the like. These additives constitute a maximum of 5% and preferably 2% by weight of the composition. The presence of a soap adversely affects the foaming characteristics of the shower gel, which requires the present gel product to be soap-free.

The pH value of the base of the foaming shower gel is in the range of 5.0 to 9.5 dependent on the formulation. Addition of hydrocarbon foaming agent to the base is not expected to change its pH value.

The post-foaming gels of present invention are prepared by forming a homogenous liquid base dispersion containing the water, the nonionic ethoxylated fatty alcohol or fatty ester, the anionic surfactant and preferably the mono- or disaccharide, and the isopropyl myristate; mixing said liquid base with the hydrocarbon foaming agent under pressure to form a post-foaming gel wherein the foaming agent is an integral part of the gel structure. The gel is maintained under pressure during the packaging into a container that will withstand pressure.

The current process for the manufacture of a post foaming shower gel involves the continuous pumping of the thin liquid base at a known rate into a system of stainless steel pipes in which the pressure is maintained at about 80–120 psi. Prior to passing through a static mixer, hydrocarbon foaming agent is also continuously dosed into the mainstream of the base at the correct level to generate a gel of the correct ratio of base to foaming agent. The mixture then passes through a static and then through a dynamic mixer by which time the blend of base and foaming agent is thoroughly mixed. At this stage the mixture may not yet be a gel but may still remain as an homogenous liquid. The mixture is then piped to a storage cylinder, while still under pressure, where the pressure inside the cylinder is again maintained at 80–90 psi. Gelling of the mixture may be immediate or may take anything up to 24 hours, depending on the formulation.

Although this is an ideal manufacturing process, it is also possible to generate a satisfactory gel by vigorously shaking all components inside a barrier pack type container, or by simple mixing of all components in any vessel which can maintain pressures.

The final gel product is stored in a pressurized cylinder until it is filled under pressure into the final package. The resultant post-foaming shower gel product may be dispensed from a pressurized aerosol container or extruded from collapsible metal tubes or the like. Packaging can be any form of barrier pack or container which will withstand pressure such as the Sepro, Conpack or Exxel packs, the Exxel being preferred. The Exxel plastic container is a self-pressurized spray container containing an inflatable rubber bag inside, which eliminates the need for an outer propellant, and can be obtained from Container Industries, Inc., Somerset, N.J.

The following examples merely illustrate the invention, but it is understood that the invention is not limited thereto. All amounts of various ingredients in the examples and elsewhere in the specification are by weight unless otherwise specified.

EXAMPLE 1

| | Post-Foaming Shower Gel % |
|---|---|
| Base Ingredients | |
| SLES[1] | 18 |
| Ethoxylated lanolin alcohol[2] | 6 |
| Sorbitol | 3 |
| Isopropyl myristate | 3 |
| Water | to 100 |
| Perfume, colour | Q.S. |
| Product Ingredients | |
| Base | 90% |
| Foaming agent | 10% |

Foaming agent is a 2:1 blend of n-pentane and iso-butane
[1]sodium lauryl ether sulfate
[2]polyoxyethylene (15) glycol ether of lanolin alcohol The water, sorbitol and the lanolin, which is a solid, are heated at a temperature of 60–65 degrees C. until the lanolin is melted and a liquid mixture is formed, the liquid is removed from the heat and agitation is started. The SLES and isopropyl myristate are added to the liquid with continued mixing. The liquid mixture is allowed to cool down to a temperature below 35 degrees C. prior to the addition of the color and perfume which is mixed until fully dispersed in said liquid. The liquid dispersion is mixed with the hydrocarbon foaming agent in a pressurized mixer to form a firm, clear, ringing shower gel which provides rapid development of profuse amounts of foam, and which feels good on the skin.

EXAMPLE 2

| Ingredients | Post-Foaming Shower Gel % |
|---|---|
| Base | |
| Polychol 15[1] | 7.00 |
| SLES 2EO (28% AI in water) | 65.00 |
| Sorbitol | 3.00 |
| Isopropyl myristate | 3.00 |
| Water | 19.90 |
| Perfume | 2.00 |
| Colour | 0.10 |

| Ingredients | Post-Foaming Shower Gel % |
|---|---|
| Finished Product | |
| Base | 90% |
| Foaming Agent | 10% |

[1]Polyoxyethylene (15) glycol ether of lanolin alcohol
Foaming agent is 2:1 blend of n-pentane and iso-butane This composition is prepared in accordance with the process of Example 1.

The final product is also a clear, firm, post-foaming shower gel capable of providing increased volume of foam which develops quickly on the skin and has a good feel.

EXAMPLES 3 AND 4

| | Post-Foaming Shower Gel | |
|---|---|---|
| Base Ingredients | 3 | 4 |
| Ethoxylated Lanolin Alcohol (Polychol 15) | 5.0 | 7.0 |
| Sodium Lauryl Ether Sulphate | 17.0 | 20.0 |
| Sorbitol - 70% solution | 2.0 | 4.0 |
| Isopropyl Myristate | 2.0 | 4.0 |
| Perfume | q.s. | (Approx. 2.0) |
| Colouring Material | | q.s. |
| Water | | to 100.0 |

Product

The above base is then blended with a 2:1 mixture of n-pentane: iso-butane, in the ratio of 90 parts base to 10 parts foaming agent.

This product is prepared in accordance with the process of Example 1.

The final product is also a clear, firm, ringing gel with rapid, voluminous foaming properties and good slip properties on the skin.

GEL FORMULATIONS

EXAMPLES 5–8

| Base Ingredients | 5 | 6 | 7 | 8 |
|---|---|---|---|---|
| SLES 2EO (28% AI in water) | 94.0 | 80.0 | 50.0 | 15.0 |
| WATER | — | 13.0 | 27.0 | 48.0 |
| PERFUME | 2.0 | 2.0 | 2.0 | 2.0 |
| POLYCHOL (15)[1] | — | 1.0 | 15.0 | 25.0 |
| IPM[2] | 2.0 | — | 3.0 | — |
| SORBITOL | 2.0 | 3.0 | 3.0 | 10.0 |
| COLOUR | QS | QS | QS | QS |

[1]Polyoxyethylene (15) glycol ether of lanolin alcohol
[2]Isopropyl myristate

The thin liquid base is gassed with 10% of a hydrocarbon blend foaming agent to complete gellation as described in Ex. 1

EXAMPLES 9–12

| Base Ingredients | 9 | 10 | 11 | 12 |
|---|---|---|---|---|
| SLES 2EO (28% AI in water) | 65.0 | 85.0 | 65.0 | 65.0 |
| WATER | 19.902 | 5.902 | 19.902 | 22.902 |
| PERFUME | 2.0 | 2.0 | 2.0 | 2.0 |
| BRIJ 30[1] | 7.0 | 1.0 | — | — |
| ATLAS G1086[2] | — | — | 7.0 | 7.0 |
| IPM | 3.0 | 3.0 | 3.0 | 3.0 |
| SORBITOL | 3.0 | 3.0 | 3.0 | — |

-continued

| Base Ingredients | 9 | 10 | 11 | 12 |
| --- | --- | --- | --- | --- |
| COLOUR | QS | QS | QS | QS |

[1] Polyoxyethylene (4) lauryl alcohol
[2] Polyoxyethylene sorbitol hexaoleate

The thin liquid base is gassed with 10% of a hydrocarbon blend foaming agent to complete gellation as described in Ex. 1.

All of the above shower gels have good high temperature stability, increased volume and speed of foaming over conventional shower products, are low viscosity bases, feel good on the skin, are readily removable from the skin by rinsing with water, and leave a soft, smooth, clean after-feel; and can be packaged in any container which will withstand pressure, in particular barrier type containers.

It is understood that the foregoing detailed description is given merely by way of illustration and that variations may be made therein without departing form the spirit of the invention.

We claim:

1. A stable, post-foaming gel shower product comprising a soap-free, surfactant-based gel composition consisting essentially of a major amount of water, about 3–23% by weight of a water-soluble anionic alkali metal $C_0$–$C_{16}$ alkyl ether sulfate surfactant, about 1–24% by weight of a water dispersible ethoxylated fatty alcohol or fatty ester, about 2–4% of isopropyl myristate, about 1–10% of a mono- or disaccharide and about 5–20% by weight of a saturated aliphatic hydrocarbon foaming agent having 4 to 5 carbon atoms as an integral part of the gel structure, the anionic surfactant and the ethoxylated fatty alcohol or ester being present in a weight ratio of about 4:1 to about 1:4.

2. The shower gel composition according to claim 1 comprising a thin liquid base consisting essentially of, by weight, about 60–75% water, about 4–26% of a water-soluble anionic surfactant, about 1–25% of a dispersible nonionic ethoxylated fatty alcohol or fatty ester, gelled with a hydrocarbon foaming agent in the weight ratio of 90% base to 10% foaming agent.

3. The gel according to claim 2, wherein the foaming agent consists of a 2:1 blend of n-pentane and iso-butane.

4. The gel according to claim 2, wherein the liquid base has a viscosity of about 100–1000 cps.

5. The gel according to claim 2, wherein the anionic surfactant is sodium lauryl ether sulfate having the formula:

$$CH_3(CH_2)_{10}CH_2(OCH_2CH_2)_nOSO_3Na$$

wherein n averages between 1 and 4.

6. The gel according to claim 2, wherein the water dispersible nonionic ethoxylated fatty alcohol is the polyethylene glycol ether of lanolin alcohol with an ethoxylation value of 15.

7. The gel according to claim 1, wherein the ethoxylated fatty alcohol is polyoxyethylene (4) lauryl alcohol.

8. The gel according to claim 1, wherein the ethoxylated fatty ester is polyoxyethylene sorbitol hexaoleate.

9. The gel according to claim 1, wherein the monosaccharide is sorbitol.

10. The gel composition according to claim 1, packaged in a container adapted to contain said gel composition under pressure, said container containing an inflatable rubber bag inside which functions as a self-pressurized spray without the use of outer propellant.

11. A gel according to claim 1, free of an outer propellant.

12. A clear or opaque, ringing to soft post-foaming gel according to claim 1, with rapid development of foam in copious amounts.

13. The method of preparing the gel of claim 2, which comprises forming a thin homogenous liquid base dispersion containing the water, the ethoxylated fatty alcohol or fatty ester, and the anionic surfactant, mixing said liquid base with the hydrocarbon foaming agent under pressure to form a post-foaming gel, wherein said foaming agent becomes an integral part of said gel structure.

14. The methhod according to claim 13, wherein the post-foaming gel is maintained under pressure during the packaging of the gel into a container that will withstand pressure.

* * * * *